United States Patent [19]
Rinne et al.

[11] Patent Number: 6,140,544
[45] Date of Patent: Oct. 31, 2000

[54] PROCESS FOR PREPARING ACETALDEHYDE FROM ETHYLENE AND OXYGEN

[75] Inventors: Bernd Rinne, Frankfurt; Erhard Franken-Stellamans, Niedernhausen, both of Germany

[73] Assignee: Celanese GmbH, Germany

[21] Appl. No.: 09/294,119

[22] Filed: Apr. 19, 1999

[30] Foreign Application Priority Data

Apr. 30, 1998 [DE] Germany .............................. 198 19 317

[51] Int. Cl.[7] .................................................. C07C 45/34
[52] U.S. Cl. ............................................. 568/475; 568/401
[58] Field of Search ...................................... 568/401, 475

[56] References Cited

FOREIGN PATENT DOCUMENTS

| | | |
|---|---|---|
| 0006523 | 1/1980 | European Pat. Off. . |
| 0438251 | 7/1991 | European Pat. Off. . |
| 1190451 | 4/1965 | Germany . |
| 2521092 | 11/1976 | Germany . |
| WO 9747372 | 12/1997 | WIPO . |

*Primary Examiner*—Sreeni Padmanabhan
*Attorney, Agent, or Firm*—Bierman, Muserlian and Lucas

[57] ABSTRACT

A process for oxidizing a reaction gas in the presence of a catalyst solution comprising a) oxidizing the reaction gas in a reactor in the presence of the catalyst solution, a reaction mixture being formed comprising droplets of the catalyst solution, b) passing the reaction gas into a first separator wherein the droplets of the catalyst solution are removed from the reaction mixture, c) passing the remaining reaction mixture from the first separator into a scrubbing apparatus wherein the oxidation product is removed from the reaction mixture, and d) passing the reaction mixture from the first separator through a second separator downstream of the first separator and upstream of a scrubbing apparatus wherein residual catalyst solution from the reaction mixture is removed.

7 Claims, 1 Drawing Sheet

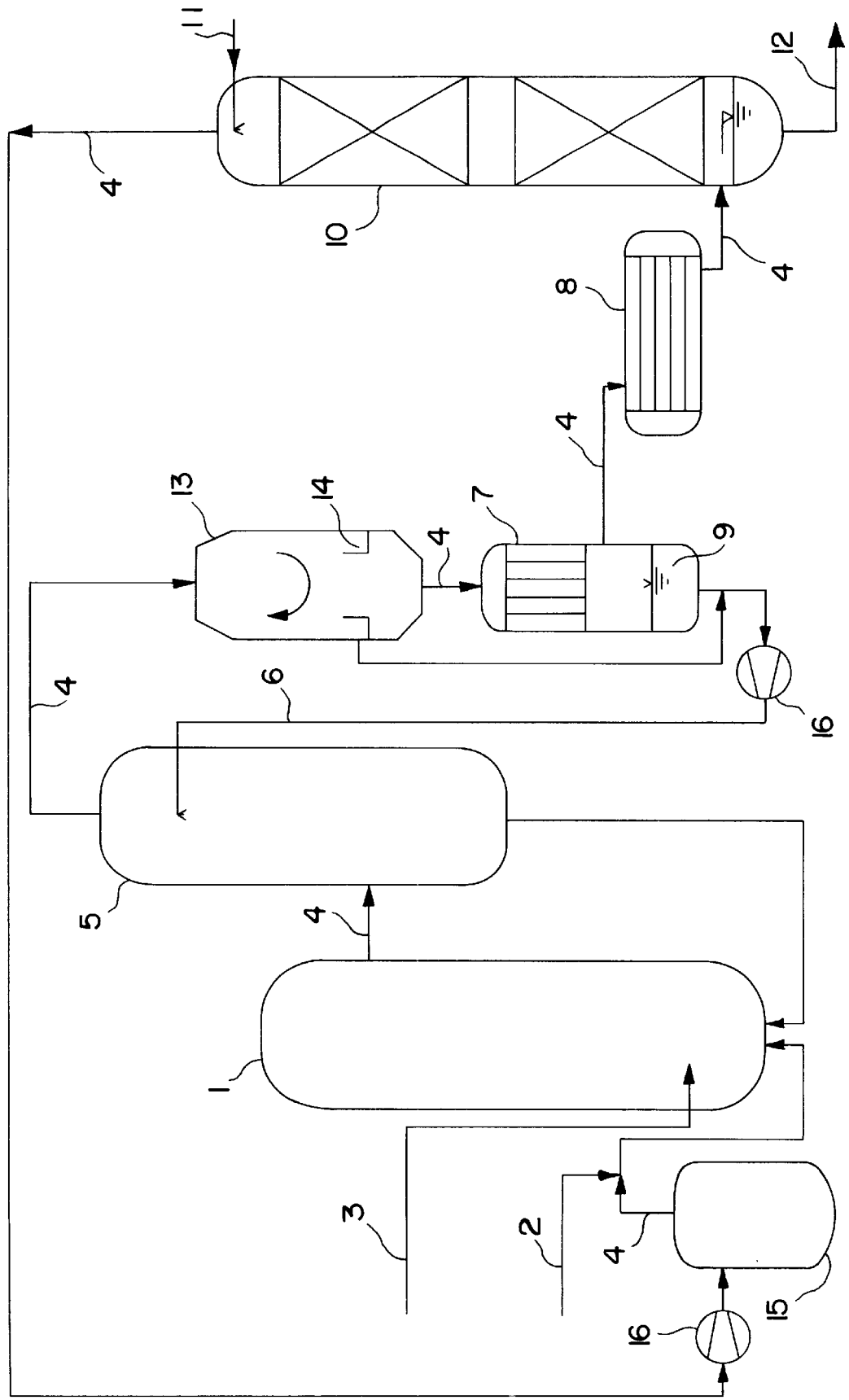

PROCESS FOR PREPARING ACETALDEHYDE FROM ETHYLENE AND OXYGEN

SUMMARY OF THE INVENTION

A process for oxidizing a reaction gas in the presence of a catalyst solution comprising
  a) oxidizing the reaction gas in a reactor in the presence of the catalyst solution to form a reaction mixture comprising droplets of the catalyst solution,
  b) passing the mixture into a first separator wherein droplets of the catalyst solution are removed from the reaction mixture, and
  c) passing the remaining reaction mixture into a scrubbing apparatus wherein the oxidation product is removed from the reaction mixture.

STATE OF THE ART

The said process is known from the prior art (DE 1 190 451) and is used for the industrial-scale preparation of aldehydes, ketones or the acids corresponding to the aldehydes by oxidizing olefins. In particular, acetaldehyde is prepared from ethylene and oxygen by this process. To catalyze the highly exothermic oxidation reaction with oxygen as oxidizing agent, usually an aqueous solution of copper chloride and palladium chloride is used.

The oxidation takes place in a reactor at the boiling point of the aqueous catalyst solution and the heat of reaction is primarily removed by evaporating water and acetaldehyde from the catalyst solution (evaporation cooling). The resultant reaction mixture essentially comprising liquid catalyst, steam, gaseous acetaldehyde and a mist of catalyst solution is passed into a first separator, which is termed a mist eliminator, in which the vapor/gas mist contents are for the most part removed from the reaction mixture, for example using scrubbing water which is injected into the mist eliminator countercurrently. The remaining reaction mixture is then cooled in heat exchangers with catalyst-containing condensate streams, some of which already have a significant acetaldehyde content, being produced, and being scrubbed out with water in a scrubbing apparatus, usually a scrubbing column, with the majority of the acetaldehyde still present in the gas phase dissolving in the water. The scrubbing phase, combined with the condensate streams distinguished by an elevated acetaldehyde concentration, is taken off for workup. The reaction mixture then remaining which still comprises small amounts of acetaldehyde is recycled to the reactor as cycle gas. Catalyst-containing condensate having only a low acetaldehyde content is used as scrubbing water for the mist eliminator.

It is a disadvantage of the known process that the catalyst separation is not complete which leads, firstly, to losses of valuable noble metal catalyst and copper, which can also disadvantageously affect the oxidation reaction, and, secondly, to increased disposal costs, since the catalyst and copper pass into the wastewater of the workup unit and have to be disposed of with this in an environmentally compatible manner.

OBJECTS OF THE INVENTION

It is an object of the invention to provide an improved process for the separation of the catalyst.

This and other objects and advantages will become obvious from the following detailed description.

THE INVENTION

The process of the invention for oxidizing a reaction gas in the presence of a catalyst solution comprises a) oxidizing the reaction gas in a reactor in the presence of the catalyst solution to form a reaction mixture comprising droplets of the catalyst solution,
  b) passing the mixture into a first separator wherein droplets of the catalyst solution are removed from the reaction mixture,
  c) passing the remaining reaction mixture from the first separator into a scrubbing apparatus to remove the oxidation product from the reaction mixture and
  d) passing the reaction mixture from the first separator through a second separator downstream of the first separator and upstream of the scrubbing apparatus to remove residual catalyst solution from the reaction mixture in the second separator.

The invention relates particularly to the corresponding process for preparing acetaldehyde from ethylene and oxygen.

The second separators used can advantageously be what are termed centrifugal separators or centrifugal mist collectors. In these, the flow of the reaction mixture is forced into a spiral path by appropriate internals such as deflection blades, so that a rotary flow is formed, as a result of which, owing to the centrifugal forces arising, droplets present in the gas stream are deposited on the outer inner wall of the separator. The deposited droplets can be collected, for example, in a surrounding channel, taken off and recycled to the first scrubbing apparatus as scrubbing water.

The solution of the invention is surprising in as far as those skilled in the art could not reckon on the gas stream from the first scrubbing apparatus arising continuously, since in exothermic reactions which are carried out under boiling conditions (evaporative cooling), greatly fluctuating gas flows are to be expected, which argues against the use of a centrifugal separator, particularly when the actual pressure drop in the separator is not known or cannot be determined as a result of such greatly variable gas flows. Accordingly, no applications are known of such separators for gas flows in the saturated vapor area, i.e. under conditions under which gas and liquid are present in equilibrium. In addition, under these conditions, the droplet size distribution is unknown and also cannot be determined. The droplets could therefore have also been too small for a successful separation.

Moreover, the disposition of the separator was chosen in opposition to the customary conditions familiar to one skilled in the art, i.e. the flow through the vertically disposed separator takes place from top to bottom. The flow therefore has a principal component in the direction of gravity. Furthermore, there was also the risk that the deflection blades would become coated with catalyst deposits, which would have impaired the acceleration of the gas flow in the peripheral direction (spin generation). It is further surprising that neither a spiral for collecting the liquid separated off nor a flushing connection are required.

The invention therefore likewise relates to the use of a centrifugal separator for separating off droplets from gas streams in the saturated vapor region.

The advantages of the process of the invention are that, inter alia, the loss of valuable noble metal catalyst and, accompanying this, the pollution of the plant wastewater with heavy metals, are decreased. Furthermore, it has been found that damage due to pitting and/or stress-cracking corrosion decreases or is avoided on those apparatuses and plant components downstream of the centrifugal separator, since less catalyst solution which strongly promotes pitting corrosion and stress-corrosion cracking passes into these plant components. Therefore, cheaper materials than hitherto can then be used for these apparatuses. In addition, fouling phenomena (deposits) decrease in the scrubbing column.

A further beneficial effect is that under otherwise identical conditions the production of acetaldehyde can be increased, for the following particular reasons: If the cycle gas stream is increased, which is beneficial from the aspect of greater production, this leads to increased foaming of the catalyst solution and thus to a markedly increased discharge of catalyst solution from the reactor to the downstream apparatuses, with said disadvantages. Using the separator of the invention, this behavior is no longer so disadvantageous, since, due to the excellent separation, the catalyst solution which is discharged more intensively can be recirculated again.

BRIEF DESCRIPTION OF THE DRAWING

FIG. 1 is an embodiment of the invention which illustrates the process flow with reference to operational experience. A restriction of the invention in any manner is not intended thereby.

The known part of the process has already been described above, for which reason only the reference numbers will be mentioned here. These are: (1) reactor, (2) ethylene, (3) oxygen, (4) reaction mixture, (5) first separator (mist eliminator), (6) scrubbing water, (7) a first cooler, (8) a second cooler, (9) catalyst-containing condensate, (10) scrubbing apparatus (scrubbing column), (11) water and (12) acetaldehyde-containing water.

According to the invention, a centrifugal separator (13) is disposed vertically as a second separator downstream of the first scrubbing apparatus (5) and upstream of the scrubbing column (10) and, preferably, upstream of the first cooler (7). In this centrifugal separator (13), the reaction mixture (4) is conducted downwards in a rotary flow (arrow) by means of deflection blades (which are not shown). The centrifugal separator (13) has a peripheral channel (14) on the interior. From this channel (14), the catalyst solution which has been separated off is removed, mixed with the catalyst-containing condensate (9) which was produced from the first cooler (7) and injected as scrubbing water (6) into the first scrubbing apparatus (5).

Operational Experience:

In a commercial industrial plant for preparing acetaldehyde from ethylene and oxygen, a centrifugal mist collector was installed according to the invention in accordance with the figure. Result: The plant capacity was increased from 120,000 metric tons per year of acetaldehyde to 135,000 metric tons per year and the pollution of wastewater from the plant by copper and palladium decreased by a factor of 50.

Various modifications of the process of the invention may be made without departing from the spirit or scope thereof and it should be understood that the invention is intended to be limited only as defined in the appended claims.

What we claim is:

1. A process for oxidizing a reaction gas in the presence of a catalyst solution comprising (a) oxidizing the reaction gas in a reactor in the presence of the catalyst solution to form a reaction mixture comprising droplets of the catalyst solution, (b) passing the mixture into a first separator wherein droplets of the catalyst solution are removed from the reaction mixture, (c) passing the remaining reaction mixture from the first separator into a scrubbing apparatus to remove the oxidation product from the reaction mixture and (d) passing the reaction mixture from the first separator through a second separator downstream of the first separator and upstream of the scrubbing apparatus to remove residual catalyst solution from the reaction mixture in the second separator wherein said separator is a centrifugal separator and has means for generating a rotary flow.

2. The process of claim 1 wherein the residual catalyst solution is separated off by conducting the reaction mixture in the second separator in a rotary flow whereby the catalyst solution droplets separate off on the inner wall of the second separator.

3. The process of claim 2 wherein, to generate the rotary flow, deflection blades are used.

4. The process of claim 1 wherein the reaction gas is an olefin.

5. The process of claim 4 wherein the olefin is ethylene.

6. The process of claim 1 wherein the means for generating a rotary flow are deflection blades.

7. The process of claim 1 wherein the second separator is a centrifugal separator for separating off droplets from gas streams in the saturated vapor region.

* * * * *